(12) United States Patent
Gilman

(10) Patent No.: US 11,000,671 B2
(45) Date of Patent: May 11, 2021

(54) MOLDED CATHETER TIP

(71) Applicant: Hollister Incorporated, Libertyville, IL (US)

(72) Inventor: Thomas H. Gilman, Spring Grove, IL (US)

(73) Assignee: Hollister Incorporated, Libertyville, IL (US)

( * ) Notice: Subject to any disclaimer, the term of this patent is extended or adjusted under 35 U.S.C. 154(b) by 412 days.

(21) Appl. No.: 15/304,427

(22) PCT Filed: Mar. 27, 2015

(86) PCT No.: PCT/US2015/023111
§ 371 (c)(1),
(2) Date: Oct. 14, 2016

(87) PCT Pub. No.: WO2015/160492
PCT Pub. Date: Oct. 22, 2015

(65) Prior Publication Data
US 2017/0035989 A1 Feb. 9, 2017

Related U.S. Application Data

(60) Provisional application No. 61/980,412, filed on Apr. 16, 2014.

(51) Int. Cl.
*A61M 25/00* (2006.01)
*B29B 11/04* (2006.01)
(Continued)

(52) U.S. Cl.
CPC ...... *A61M 25/0069* (2013.01); *A61M 25/001* (2013.01); *A61M 25/0045* (2013.01);
(Continued)

(58) Field of Classification Search
CPC ............ A61M 25/001; A61M 25/0045; A61M 25/0067; A61M 25/0068; A61M 25/0069
See application file for complete search history.

(56) References Cited

U.S. PATENT DOCUMENTS 3,288,901 A 11/1966 Clark
3,865,666 A 2/1975 Shoney
(Continued)

FOREIGN PATENT DOCUMENTS

GB 2 003 050 3/1979
GB 2 065 480 7/1981

OTHER PUBLICATIONS

International Search Report and Written Opinion for PCT/US2015/023111 dated Sep. 1, 2015.
(Continued)

*Primary Examiner* — Kai H Weng
(74) *Attorney, Agent, or Firm* — Cook Alex Ltd.

(57) ABSTRACT

A catheter has extruded length of tubing and an injection molded tip that facilitates insertion of the catheter into the body. The catheter is fabricated by the steps of providing the tubing, for example, by extruding the tubing from a thermoplastic resin cutting the tubing to the desired length, inserting a plug into the tubing, inserting one end of the tubing into an injection mold cavity, creating and forming a tip in an injection molding step, and demolding the tubing with the formed tip.

19 Claims, 2 Drawing Sheets

(51) Int. Cl.
    *B29C 45/14*      (2006.01)
    *B29K 101/12*      (2006.01)
    *B29K 105/20*      (2006.01)
    *B29L 31/00*      (2006.01)

(52) U.S. Cl.
    CPC .... *A61M 25/0067* (2013.01); *A61M 25/0068* (2013.01); *B29B 11/04* (2013.01); *B29C 45/14426* (2013.01); *B29K 2101/12* (2013.01); *B29K 2105/20* (2013.01); *B29L 2031/7542* (2013.01)

(56) References Cited

U.S. PATENT DOCUMENTS

| | | | |
|---|---|---|---|
| 3,901,965 A | | 8/1975 | Honeyman, III |
| 4,210,478 A | | 7/1980 | Shoney |
| 4,244,713 A | * | 1/1981 | Goodwin .......... A61B 5/02042 600/309 |
| 4,900,303 A | | 2/1990 | Lemelson |
| 5,084,033 A | | 1/1992 | O'Neill et al. |
| 5,409,652 A | | 4/1995 | Carter |
| 5,630,794 A | | 5/1997 | Lax et al. |
| 5,762,637 A | | 6/1998 | Berg et al. |
| 5,810,789 A | | 9/1998 | Powers et al. |
| 6,332,877 B1 | * | 12/2001 | Michels ................ A61L 29/043 604/263 |
| 6,964,750 B2 | | 11/2005 | Fulford |
| 7,655,000 B2 | | 2/2010 | Walls et al. |
| 7,943,077 B2 | | 5/2011 | Sansoucy |
| 7,988,658 B2 | | 8/2011 | Quinn |
| 8,048,058 B2 | | 11/2011 | Fulford |
| 8,066,693 B2 | | 11/2011 | Tanghoj et al. |
| 8,123,892 B2 | | 2/2012 | Morris et al. |
| 8,257,635 B2 | | 9/2012 | Sansoucy |
| 2005/0165382 A1 | | 7/2005 | Fulford |
| 2006/0100572 A1 | | 5/2006 | DiMatteo et al. |
| 2009/0234227 A1 | | 9/2009 | Punga |
| 2009/0306608 A1 | * | 12/2009 | Li .......... A61F 9/0017 604/294 |
| 2010/0198195 A1 | * | 8/2010 | Nishtala ........... A61M 25/0668 604/544 |
| 2010/0274224 A1 | * | 10/2010 | Jain .......... A61F 9/0017 604/514 |
| 2011/0098683 A1 | * | 4/2011 | Wiita ................ A61M 25/1002 604/544 |
| 2013/0150828 A1 | | 6/2013 | Conway |
| 2013/0289467 A1 | * | 10/2013 | Haffner ............ A61F 9/00781 604/8 |

OTHER PUBLICATIONS

Canadian Office Action for Canadian Patent Application No. 2,945,972 entitled: Molded Catheter Tip, dated Apr. 1, 2020 pp. 1-7.

\* cited by examiner

MOLDED CATHETER TIP

CROSS REFERENCE TO RELATED APPLICATION

This application is the U.S. National Stage of PCT International Patent Application No. PCT/US2015/023111, filed Mar. 27, 2015, which claims the benefit of U.S. Provisional Patent Application Ser. No. 61/980,412, filed Apr. 16, 2014, the disclosure of which is incorporated by reference herein.

FIELD OF THE DISCLOSURE

The present disclosure is directed generally to a catheter assembly and a method of making a catheter assembly.

BACKGROUND

A catheter is a flexible, hollow tube which can be inserted into the body for the introduction or removal of fluids. A common, but by no means exclusive, type of catheter is a urinary catheter which is used by those who suffer from various abnormalities of the urinary system. A urinary catheter is inserted through the urethra for draining urine from the bladder.

To facilitate insertion of a catheter into a body cavity, it is desirable to have a formed tip on one end of the catheter tube. A very common way to make this structure is to extrude tubing from a thermoplastic polymer material, and cut it to the desired length. One of the cut ends is then formed into a tip shape in a secondary operation, for example, by forcing the cut end into a heated die that has the desired tip shape.

Extruding the tubing section of the catheter is desirable because it is a relatively inexpensive process, and it allows for good control of the tube's outside diameter and wall thickness. Forming a tip by pushing a tube cut end into a heated die has some disadvantages, however. The die must be hot during the pushing step, in order to soften the tube material so it will form. Then the die must be cooled to allow release of the formed part. For the next cycle, the die must now be reheated. These die heating and cooling steps limit how short the process cycle time can be. Another problem with the heated die forming method concerns catheters having multiple layers. It is desirable to have a hydrophilic coating on the exterior of the catheter to add lubricity. Such coatings are not compatible with all tube materials so it is known to co-extrude the tubing from two layers of different materials, the outer of which readily accepts a hydrophilic coating. The coating is applied after formation of the tip. A problem with the heated die tip formation method arises because the heating process distorts the layers at the end of the tube. The desired outer layer material, which accepts the coating, may not remain on the outside of the tip after heated die formation of the tip. That is, the inner and outer tubing layers tend to become somewhat distorted during heated die tip formation with the result that some of the inner tubing layer material may end up exposed on the exterior of the formed tip. This can lead to failure of the hydrophilic coating to adhere fully to the tip.

SUMMARY

In one aspect, the present disclosure concerns a catheter whose shaft is formed from a tube, such as, for example, an extruded tube. A formed tip that facilitates insertion of the catheter into the body is fabricated on one end of the tube by an insert molding process.

A catheter for introduction into a body cavity may be fabricated by the following steps: 1) a tube is extruded from a thermoplastic polymer material, and cut to the desired catheter length; 2) one end of the length of tubing is inserted into an injection mold cavity; 3) a formed tip is created and bonded to the tubing end in an injection molding step; 4) the tubing with the formed tip is demolded; and 5) if desired, a funnel can be attached to the other end of the tubing by conventional methods such as solvent bonding, spin welding, hot melt bonding, or by the non-conventional step of injection molding the funnel onto the tubing.

The mold for the tip formation can be gated at the apex of the tip, and a small depression can be designed into this apex so that any gate residue in the formed part is not protruding from the surface of the part.

The injection molding steps are further characterized in that a plug is press fit into the lumen at one end of the tubing just prior to inserting that end into the injection mold. During the injection molding step that forms the tip on the end of the tube the plug acts as a molding shut-off to ensure proper filling of the mold. In one alternative embodiment the plug can be pre-heated, to reduce the amount of heat transfer from the injected thermoplastic polymer material needed for proper bonding to the plug and to the tubing walls.

In total this is a novel way to provide a formed tip on the end of an extruded tube. The strategy of using a thermoplastic plug as a pre-molding insert to provide injection shut-off is believed to be novel. The idea of injection molding on to a pre-heated plug, as an aid to good bonding, is believed to be novel as well. The injection-molded tip also maintains the integrity of a multi-layer tube construction, assuring that the outer layer material of the tubing remains on the exterior of the catheter where it can accept a hydrophilic coating.

DETAILED DESCRIPTION OF THE EMBODIMENTS

Figure 1:
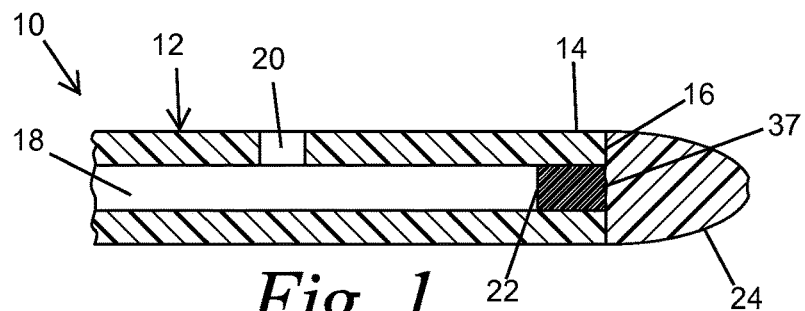
FIG. 1 is a longitudinal cross-sectional view of an end portion of a tubing and tip of a catheter assembly according to the present disclosure.

The present disclosure is directed to a catheter and a method of making it, the method including the steps of cutting tubing to the desired length, inserting a plug into one end of the tubing and injection molding a tip onto the plugged end of the tubing. FIG. 1 illustrates an end portion of the catheter 10 according to the present disclosure. The catheter 10 has tubing 12 which is cut to length to define an end portion 14 which terminates at a radial end face 16. Tubing 12 may be made by any suitable process, such as, for example, by an extrusion process. As is conventional, the tubing 12 defines an axial lumen 18 that extends throughout the length of the tubing 12. There is also a radial eyelet 20 defined in one wall and in communication with the lumen 18. For a urinary catheter, lumen 18 would serve as a urinary lumen with urine draining into the lumen 18 through the eyelet 20. A plug 22 is provided of a suitable material, e.g., the main tubing wall component material. The plug 22 is sized to be insertable into the tubing lumen 18 with an interference fit. In its simplest form, the plug 22 can be a cut length of an extruded rod that is just larger in diameter than the tubing lumen 18. In an alternative form, the plug can be a micro-injection molded part, and can have a taper on one end, or preferably on both ends, to aid in the insertion process. In embodiments wherein the plug has one or more tapered portions, it will be understood that a portion of the plug 22 will have a maximum outer diameter at least as large as the inside diameter of the lumen 18, thus assuring the lumen 18 will be completely blocked during injection molding of the tip 24.

Figure 4:
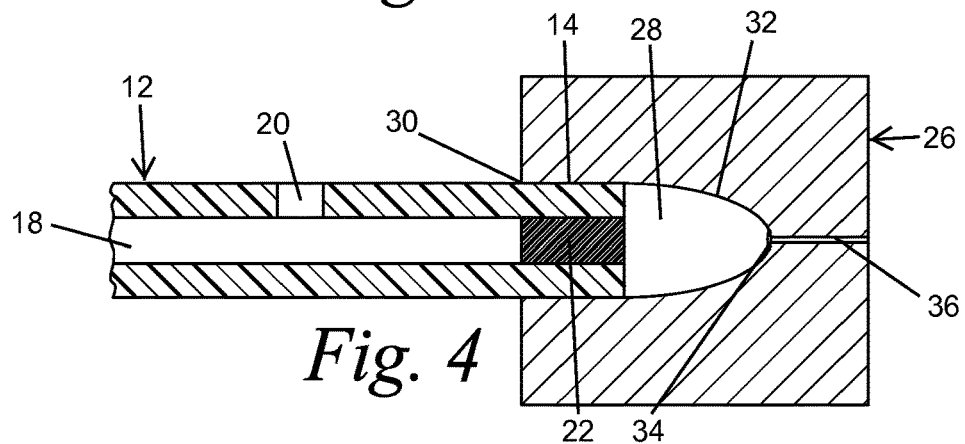
FIG. 4 is a diagrammatic cross-sectional view of a tubing end portion and plug inserted into the cavity of a mold, ready for injection molding of the tip.

The plug 22 may be inserted into the lumen 18 at the end portion 14 of the tubing 12. This end portion 14 is inserted into an injection mold. A formed tip 24 is then injection molded onto the end portion 14 of the tubing 12 using a mold as shown in FIG. 4. In FIG. 4 the end portion 14 of the tubing 12 is inserted into a mold. A first half of the mold is shown at 26. It will be understood that a second mold half, not shown but largely a mirror image of the first mold half (with the mirror plane being the plane of the paper of the drawing), would be used in the injection molding process, although preferably the mold halves are integral. That is, they are not necessarily made to be separable, although they could be. Together the mold halves define a cavity 28. The cavity 28 opens to the exterior of the mold at an opening 30 for receiving the end portion 14 of the tubing 12. The cavity 28 has an inner surface 32 that has the size and shape of the finished tip 24. Surface 32 optionally includes a slight bulge at 34 that will create a depression in the extreme end of the tip 24 as will be explained further below. A sprue 36 extends through the mold and forms a passageway through which molten thermoplastic polymer material can be introduced into the cavity 28.

When molten thermoplastic polymer material is injected into the cavity 28 the plug 22 and radial end face 16 serve as a stop for the injected thermoplastic polymer material; in a sense the plug 22 and end face 16 become one wall of the injection mold while the inner surface 32 forms the other wall. This ensures that the mold cavity 28 will fill properly, resulting in a well formed tip 24 of controlled geometry.

The material for injection molding should be one that is compatible with the tubing material, to ensure good bonding between the molded tip 24 and the tubing 12. Because the plug 22 is made of a suitable material, with proper selection of injection molding parameters, a strong bond forms between the plug 22 and the injected tip material along a plug-to-tip bond line 37. Likewise a strong bond forms between the injected tip material and the end face 16 of the tubing 12. After the injected tip material cools, optionally the mold halves are separated and the tubing and tip are removed from the cavity 28. Alternatively, the mold may be one piece, and the tubing 12 with tip 24 may just be pulled free of the mold. The result is a formed tip 24 of desired geometry that is integral with the end 14 of the tubing 12.

In one alternate embodiment of the process, the plug 22 is pre-heated before inserting it into the tubing end 14, just prior to insertion of the tube into the injection mold. The plug will then provide a source of heat to heat the tubing walls, and in all less heat transfer from the injected thermoplastic polymer material will be needed to create the desired good bonding between the injected thermoplastic polymer material tip, the plug, and the tubing end face. Using the strategy of pre-heating the plug will reduce the melt temperature required to ensure good bonding between the injected thermoplastic polymer material tip, the plug, and the tubing end face, and may also reduce the required cycle time for the tip molding process.

Figure 2:
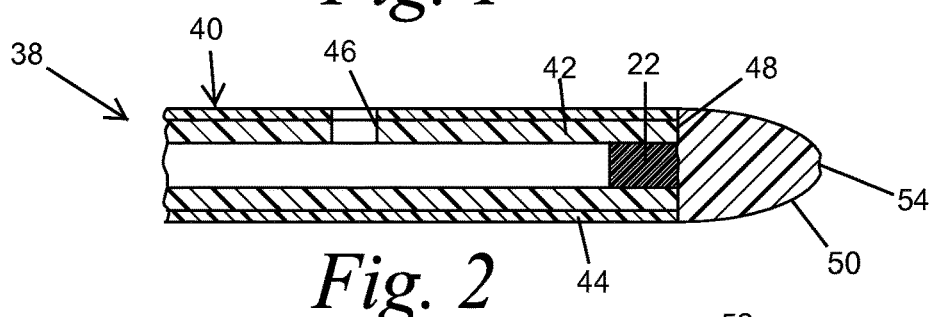
FIG. 2 is a cross-sectional view similar to FIG. 1 showing an alternate embodiment of the tubing which has a dual layer construction.

FIG. 2 illustrates an alternate embodiment of a catheter 38 having a different kind of tubing. In this embodiment the tubing 40 has a dual layer construction including an inner wall 42 and an outer wall 44. The tubing 40 may be made by coextrusion wherein inner wall 42 and outer wall 44 are different materials. Eyelet 46 extends through both walls. The radial end face 48 includes both walls and is covered by the tip 50. In this embodiment, the outer wall 44, the plug 22 and the tip 50 may be made of the same or similar materials. Alternatively, the plug 22 may be made of material the same or similar to that of the inner wall 42.

Figure 3:
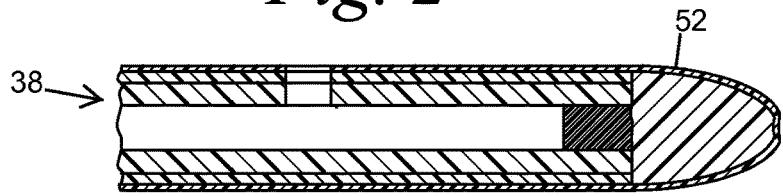
FIG. 3 is a cross-sectional view similar to FIG. 2 showing an alternate embodiment further including a hydrophilic coating.

FIG. 3 shows an alternate embodiment wherein the catheter 38 of FIG. 2 has added to it an outer hydrophilic coating 52. The coating 52 surrounds both the outer wall 44 and the tip 50. The coating 52 may be of the type commonly used to increase the lubricity of the catheter. The tip material is preferably the same as the outer wall material so they will both accept the outer hydrophilic coating 52.

Figure 5:
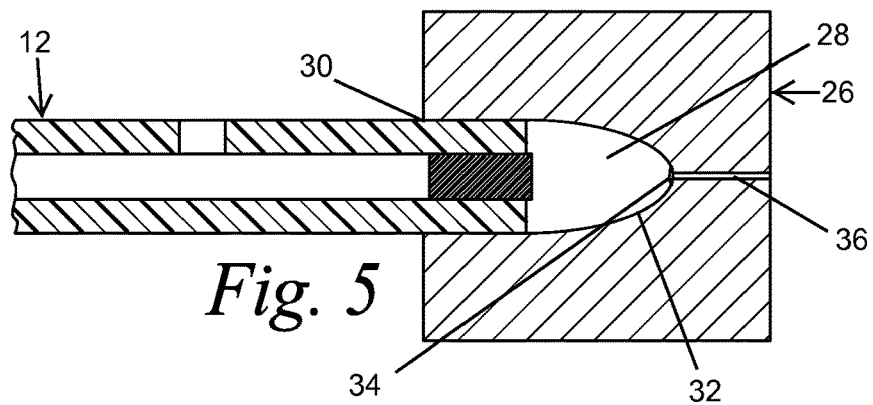
FIG. 5 is a cross-sectional view similar to FIG. 4 showing an alternate, slightly protruding axial position for the plug.
Figure 6:
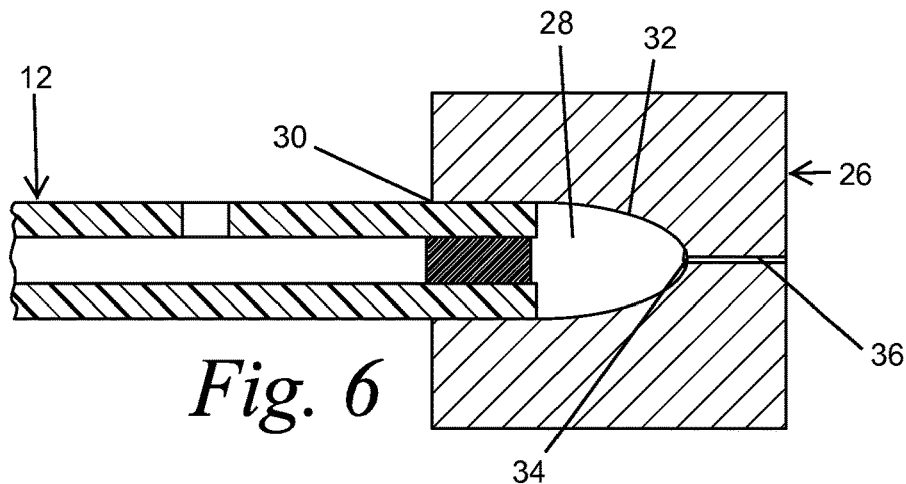
FIG. 6 is a cross-sectional view similar to FIG. 4 showing a further alternate, slightly recessed axial position for the plug.

FIGS. 5 and 6 are similar to FIG. 4 but show alternate axial positions for the plug 22. In FIG. 5 the plug 22 protrudes axially beyond the radial end face 16. In FIG. 6 the plug 22 is recessed somewhat from the radial end face 16.

Figure 7:
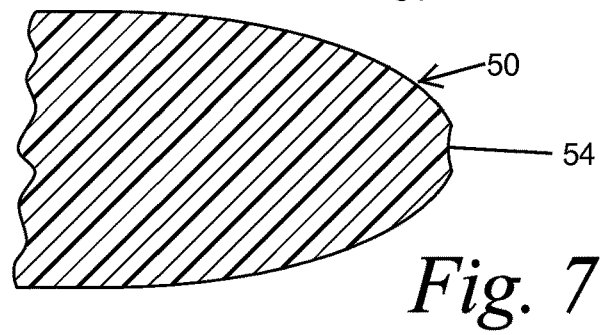
FIG. 7 is a cross-sectional view of a tip on an enlarged scale to illustrate the depression in the end of the tip.

In the enlarged view of FIG. 7 it can be seen that the bulge 34 in the mold cavity's inner surface 32 creates a dimple or depression 54 in the apex of the tip 24. Since the sprue 36 is gated at the apex of the tip, any gate residue in the formed tip is not protruding from the surface of the tip but instead lies within the depression 54 where it will not affect a user of the catheter.

Figure 8:
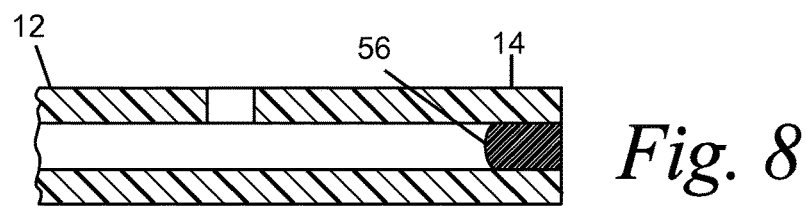
FIGS. 8, 9 and 10 are cross-sectional views through an end portion of tubing prior to injection molding but after insertion of a plug, each showing an alternate embodiment of a plug shape.
Figure 9:
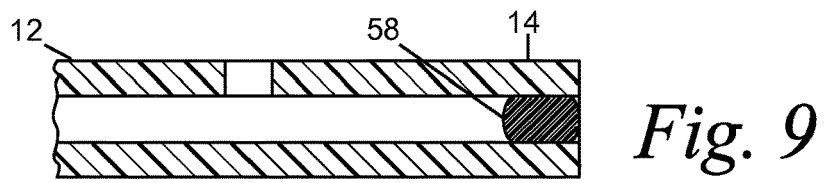
Figure 10:
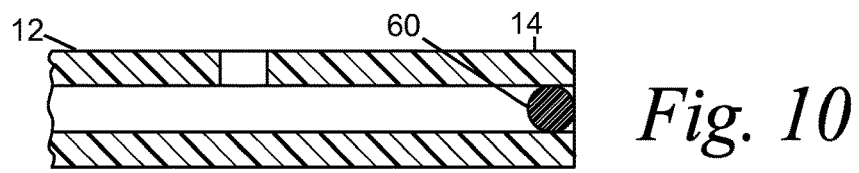

FIGS. 8, 9 and 10 illustrate alternate forms that the plug could take. FIG. 8 shows a plug 56 having a rounded inner end that assists with insertion into the lumen 18 of the tubing 12. FIG. 9 shows a plug 58 that is rounded on both ends so either one can be readily inserted into the lumen. FIG. 10 shows a spherical plug 60.

Figure 11:
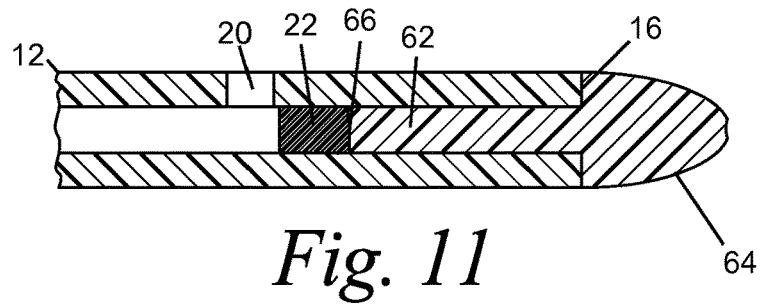
FIG. 11 is a cross-sectional view similar to FIG. 1, showing a further alternate embodiment having a plug located at an axial position well recessed from the end face of the tubing, the plug location permitting formation of a stubshaft on the tip.

FIG. 11 shows yet another alternate embodiment wherein prior to molding the plug 22 is axially recessed into the lumen nearly to the eyelet 20. With this axial placement of the plug injected thermoplastic polymer material will enter the lumen until it meets the plug 22, thereby forming a stubshaft 62 that is integral with the tip 64. This provides enhanced stability of the tip on the tubing 12. The stubshaft 62 joins the plug at the plug-to-tip bond line 66.

The mold desirably does not have any parting line, rather the part will demold due to the taper of the tip and material shrinkage on cooling. A possible alternate configuration during the molding step is to have the long axis of the tube protruding from the mold vertically. In this configuration gravity will help to accomplish the desired result of the mold filling before thermoplastic polymer material enters the tube lumen. The amount of injected thermoplastic polymer material entering the tube lumen is then controlled by controlling molding shot size.

In the catheter of the present disclosure the thermoplastic polymer material that will be injection molded to the end of the extruded tube can be kept always hot, in the molder feed system. A mold cooling step is needed, but only the heat transferred to the mold by the injected thermoplastic polymer material needs to be carried away. This will result in a shorter cycle time compared to the conventional tip forming process.

Another advantage of the catheter of the present disclosure is that the total length of the tipped catheter can be highly controlled. In the conventional process, the tip formed on the end of the tubing will have a much higher length variation. This variability in the tipped catheter length can cause problems in subsequent catheter converting steps.

A further advantage of the catheter of the present disclosure is that the proposed process will work well with coextruded tubing, such as shown in FIG. 2 for example. This tubing 40 may have a thin outer wall 44 present for accepting a hydrophilic coating, such as at 52 in FIG. 3. In such an embodiment, the inner wall 42 may be made from a material that has desirable mechanical characteristics for a urinary catheter, e.g., desired stiffness/flexibility, such materials may include for example thermoplastic resins such as olefins, particularly polyethylenes, polypropylenes, polyvinylchlorides, polytetrafluoroethylenes, polyvinylacetates, polystyrenes, polyesters, polyurethane, polyamides, ethylene vinyl acetate copolymers, copolymers of ethylene with other comonomers such as acrylic acid, or combinations thereof. The outer wall 44 and tip 50 may be made from a material that is conducive to bonding or receiving the hydrophilic coating. The outer wall 44 and tip 50 may be for example made from a water-swellable polymer such as water-swellable polyamide-base copolymers, water-swellable polyester-based copolymers or water-swellable urethane-based copolymers. Other polymers may include blends of these water swellable thermoplastic polymers with non-water swellable thermoplastic polymers. Polymers can be utilized that have functional groups selected to provide bonding to specific coating chemistries. Functional groups such as carboxyl, amine, hydroxyl, and other known reactive groups can be appropriate, depending on the coating choice. The hydrophilic coating may be any coating that bonds or attaches to the outer wall 44 and tip 50. The hydrophilic coating may be bond to outer wall 44 by any suitable, manner of attachment, such as physical anchoring via an interpenetrating polymer network or by chemical bonding. Such hydrophilic coatings may include for example, polyvinylpyrollidone, polyacrylic acid, polyvinylether maleic anhydride copolymer, or other highly hydrophilic polymers and copolymers. In the conventional forming process, the process conditions need to be adjusted and controlled to keep the desired outer layer material on the surface of the formed tip.

It is believed that this process of tip forming will be a lower cost option compared to conventional forming with an induction heated die.

An alternate embodiment of the catheter of the present disclosure has an extruded tube that is cut to length for a catheter product. At one cut end, a formed tip is made by an insert micro-injection molding step as described above. At the other end, a funnel is formed by a second insert injection molding step. Prior art catheters having a funnel are made by cutting an extruded tube to length, forming a tip by forcing one of the cut ends into a heated die, followed by cooling of the die. Separately a funnel part is injection molded. Finally, the funnel part is assembled to the other tube end using solvent bonding. These tip forming steps and the funnel solvent bonding steps involve a fair amount of labor cost, which is avoided by making the funnel-equipped catheter according to the present disclosure. The insert injection molded funnel can comprise less material compared to a conventional injection molded funnel that is assembled to an extruded tube. The methods described in this disclosure are more generally applicable to use of other materials, such as coextruded tubes and materials that do not solvent bond well. Together these can provide a fully converted catheter product, at meaningful cost savings.

It should be understood that various changes and modifications to the presently preferred embodiments described herein will be apparent to those skilled in the art. Such changes and modification can be made without departing from the spirit and scope of the invention disclosed herein.

Aspects of the present subject matter described above may be beneficial alone or in combination with one or more other aspects. Without limiting the foregoing description, in accordance with one aspect of the subject matter herein, there is provided a catheter, which includes a length of tubing with an axial lumen defined therein. The lumen has an inside diameter and the tubing terminates at an end. A plug is inserted in the lumen a distance sufficient to axially recess the plug from the end of the tubing. At least a portion of the plug has a maximum outside diameter at least as large as the inside diameter of the lumen. A tip is attached to an end of the tubing. The tip includes a stubshaft that extends into the lumen and is joined to the plug at a plug-to-tip bond line.

In accordance with another aspect which may be used or combined with the preceding aspect, the catheter of has a hydrophilic coating on the exterior surface of the tubing and tip.

In accordance with another aspect which may be used or combined with any of the preceding aspects, the catheter is provided with tubing that has an inner wall and an outer wall.

In accordance with another aspect which may be used or combined with any of the preceding aspects, the tubing has an inner wall and an outer wall and further includes a hydrophilic coating on the exterior surface of the outer wall and tip.

In accordance with another aspect which may be used or combined with any of the preceding aspects, the plug has at least one tapered end.

In accordance with another aspect which may be used or combined with any of the preceding aspects, the tip has an apex at the free end thereof with a depression formed in the apex.

In accordance with another aspect, there is provided a catheter, which includes a length of tubing with an axial lumen defined therein. The lumen has an inside diameter, and the tubing terminates at an end. A plug is inserted in the lumen. At least a portion of the plug has a maximum outside diameter at least as large as the inside diameter of the lumen. A tip is attached to an end of the tubing. The tip has an apex at its end opposite the tubing end, with a depression formed in the apex.

In accordance with another aspect which may be used or combined with the preceding aspect, the catheter tubing has an inner wall and an outer wall and a hydrophilic coating on the exterior surface of the outer wall and tip.

In accordance with another aspect, there is provided a method of making a catheter, including the steps of providing tubing having an axial lumen defined therein, the lumen having an inside diameter; cutting the tubing to the desired catheter length; forming a plug, at least a portion of the plug having an outside diameter at least as large as the inside diameter of the lumen; pre-heating the plug; inserting the pre-heated plug into the lumen at an end of the tubing; inserting the end of the tubing into an injection mold cavity; injecting molten thermoplastic polymer material under pressure into the mold cavity; cooling the mold cavity so the molten thermoplastic polymer material solidifies and forms a tip bonded to the plug and to the tubing end; and removing the tubing with the formed tip from the mold.

In another aspect which may be used or combined with the preceding aspect, the method may include the step of forming a depression in the apex of the tip.

In accordance with another aspect which may be used or combined with any of the preceding two aspects, the step of inserting the pre-heated plug into the lumen may be characterized by locating the plug so that its outer end terminates flush with the end of the tubing.

In accordance with another aspect which may be used or combined with any of the preceding ninth and tenth aspects, the step of inserting the pre-heated plug into the lumen is characterized by recessing the plug from the end of the tubing.

In accordance with another aspect, there is provided a method of making a catheter, including the steps of providing tubing having an axial lumen defined therein, the lumen having an inside diameter and the tubing having an inner wall and an outer wall; cutting the tubing to the desired catheter length; forming a plug, at least a portion of the plug having an outside diameter at least as large as the inside diameter of the lumen; inserting the plug into the lumen at an end of the tubing; inserting the end of the tubing into an injection mold cavity; injecting molten thermoplastic polymer material under pressure into the mold cavity; cooling the mold cavity so the molten thermoplastic polymer material solidifies and forms a tip bonded to the plug and to the tubing end; removing the tubing with the formed tip from the mold; and applying a hydrophilic coating to the exterior of the tubing and tip.

In accordance with another aspect which may be used or combined with the preceding aspect, the step of forming a depression in the apex of the tip.

In accordance with another aspect which may be used or combined with any of the preceding two aspects, pre-heating the plug prior to inserting it into the lumen.

In accordance with another aspect which may be used or combined with any of the preceding three aspects, the step of inserting the pre-heated plug into the lumen is characterized by locating the plug so that its outer end terminates flush with the end of the tubing.

In accordance with another aspect which may be used or combined with any of the second, third and fourth preceding aspects, the step of inserting the pre-heated plug into the lumen is characterized by recessing the plug from the end of the tubing.

In accordance with another aspect, there is provided a urinary catheter, which includes a length of tubing with an axial urinary lumen defined therein, the lumen having an inside diameter, and the tubing terminating at an end. A plug is inserted in the urinary lumen, at least a portion of the plug having a maximum outside diameter at least as large as the inside diameter of the urinary lumen. A tip is attached to an end of the tubing, and is joined to the plug at a plug-to-tip bond line.

In accordance with another aspect which may be used or combined with the preceding aspect, the plug terminates at the same location as the tubing end.

In accordance with another aspect which may be used or combined with the second preceding aspect, the plug may protrude from the tubing end.

In accordance with another aspect which may be used or combined with the third preceding aspect, the plug may be axially recessed from the tubing end.

The invention claimed is:

1. A urinary catheter, comprising:
    a urinary catheter shaft having a length of polymer tubing made from a polymer material, the length of polymer tubing having an axial lumen defined therein, the lumen having an inside diameter, the polymer tubing terminating at an end;
    a non-porous polymer plug inserted in the lumen a distance sufficient to axially recess the polymer plug from the end of the polymer tubing, at least a portion of the polymer plug having a maximum outside diameter at least as large as the inside diameter of the lumen, the polymer plug having a length wherein the polymer plug is in direct contact with the polymer material of the polymer tubing at least along a portion of the length of the polymer plug; and
    a tip attached to an end of the polymer tubing, the tip including a stubshaft that extends into the lumen and is bonded to the polymer plug at a plug-to-tip bond line.

2. The urinary catheter of claim 1 further comprising a hydrophilic coating on an exterior surface of the polymer tubing and tip.

3. The urinary catheter of claim 1 wherein the polymer tubing has an inner wall and an outer wall.

4. The urinary catheter of claim 1 wherein the polymer tubing has an inner wall and an outer wall and further comprising a hydrophilic coating on an exterior surface of the outer wall and tip.

5. The urinary catheter of claim 1 wherein the polymer plug has at least one tapered end.

6. The urinary catheter of claim 1 wherein the tip has an apex at a free end thereof with a depression formed in the apex.

7. The urinary catheter of claim 1, wherein the plug is a solid material.

8. The urinary catheter of claim 1, wherein the tip is a solid material.

9. The urinary catheter of claim 1, wherein the tip is a non-porous material.

10. The urinary catheter of claim 3, wherein the plug and the inner wall are comprised of the same material.

11. The urinary catheter of claim 3, wherein the plug, the tip and the outer wall are comprised of the same material.

12. The urinary catheter of claim 3, wherein the plug and the inner wall are comprised of a similar material.

13. The urinary catheter of claim 3, wherein the plug, the tip and the outer wall are comprised of a similar material.

14. The urinary catheter of claim 3, wherein the outer wall is comprised of at least one of the group including polyethylenes, polypropylenes, polyvinylchlorides, polytetrafluoroethylenes, polyvinylacetates, polystyrenes, polyesters, polyurethane, polyamides, ethylene vinyl acetate copolymers, copolymers of ethylene with other comonomers such as acrylic acid, or combinations thereof.

15. The urinary catheter of claim 3, wherein the outer wall comprises a water swellable polymer.

16. The urinary catheter of claim 3, wherein the tip comprises a water swellable polymer.

17. The urinary catheter of claim 1, wherein the tip is integral with the end of the tubing.

18. The urinary catheter of claim 1, wherein the tip and the end face of the tubing exhibit a strong bond.

19. The urinary catheter of claim 1, wherein the tip is formed by injection molding.

\* \* \* \* \*